(12) United States Patent
Chin

(10) Patent No.: US 6,418,934 B1
(45) Date of Patent: Jul. 16, 2002

(54) USE OF POLYMERIC MATERIALS FOR ENLARGING HUMAN GLANS AND METHOD OF PERFORMING A SURGERY FOR ENLARGING A HUMAN GLANS WITH THE SAID MATERIALS

(76) Inventor: Sae-Hoon Chin, #24-801, Sampoong Apt., 1685, Seocho-dong, Seocho-gu, 135-070, Seoul (KR)

( * ) Notice: Subject to any disclaimer, the term of this patent is extended or adjusted under 35 U.S.C. 154(b) by 34 days.

(21) Appl. No.: 09/628,797
(22) Filed: Jul. 28, 2000
(30) Foreign Application Priority Data Apr. 19, 2000 (KR) .................................. 00-20547

(51) Int. Cl.$^7$ .............................. A61B 19/00; A61F 5/00
(52) U.S. Cl. ........................................... 128/898; 600/40
(58) Field of Search ....................... 600/38, 40; 128/898

(56) References Cited

U.S. PATENT DOCUMENTS

| | | | | |
|---|---|---|---|---|
| 4,558,693 A | * | 12/1985 | Lash et al. ..................... | 600/40 |
| 6,173,714 B1 | * | 1/2001 | Cho ............................ | 128/898 |

FOREIGN PATENT DOCUMENTS

| | | | | |
|---|---|---|---|---|
| DE | WO 99/18897 | * | 4/1999 | ............. A61F/5/41 |

OTHER PUBLICATIONS

Abstract for Ghanem HM, Fahmy I, el–Meliegy A; "Malleable penile implants without plaque surgery in the treatment of Peyronie's disease"; Sep. 1998; Int J Impot Res; 10(3); pp. 171–173.*

Abstract for Subrini L.; "Flexible penile implants in the restoration of erectile function"; 1993; Ann Urol (paris); 27(3); pp. 183–191.*

Abstract for Smith CP, Kraus SR, Boone TB; "Managemnt of impending penile prosthesis erosion with a plytetrafluoroethylene distal wind sock graft"; Dec. 1998; J Urol; 160(6 Pt 1); pp. 2037–2040.*

Abstract for Subrini L; "Flexible penile implants. An experience over 60 cases"; Feb. 1994; Ann Chir Plast Esthet; 39(1); pp. 15–26.*

* cited by examiner

Primary Examiner—Eric F. Winakur
Assistant Examiner—Nikita R Veniaminov
(74) Attorney, Agent, or Firm—Robin L. Teskin

(57) ABSTRACT

The present invention relates to the use of polymeric materials for enlarging the glans of the male genital organ and the method of performing a surgery for enlarging the glans of the male genital organ with any of the said material. A material selected from the group consisting of collagen, hyaluronic acid, artecoll, dermalive, zyplast, restylane and perlane can be used for the said purpose. In case any of the said materials is transplanted into the lamina propria mucosae so that the transplanted material may be 0.5 mm~3.0 mm thick, there are no evidence of erectile disfunction even after such transplantation. A man whose glans is enlarged through the said transplantation can have sexual confidence and satisfaction and further give a great sexual satisfaction to his female mate.

3 Claims, 1 Drawing Sheet

Figure 1:
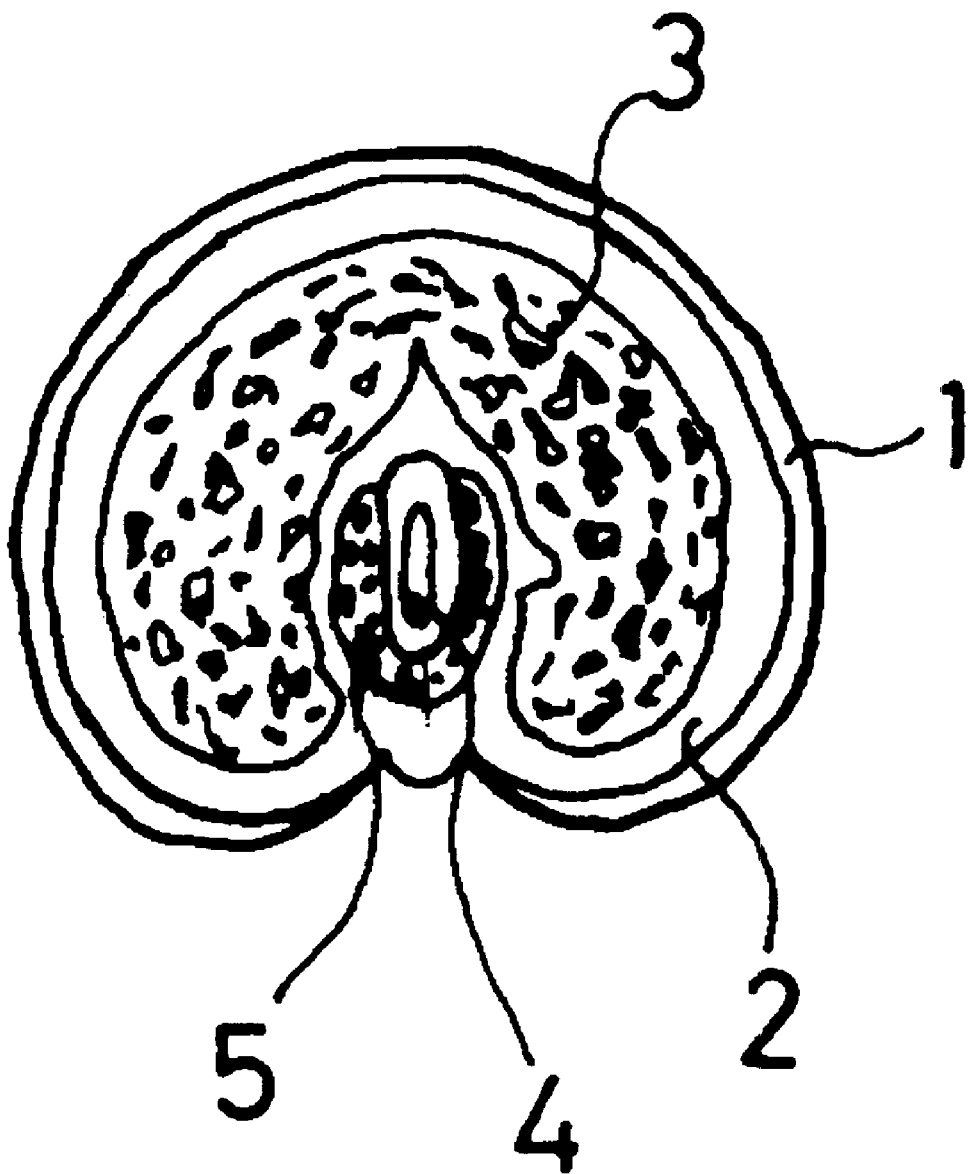

USE OF POLYMERIC MATERIALS FOR ENLARGING HUMAN GLANS AND METHOD OF PERFORMING A SURGERY FOR ENLARGING A HUMAN GLANS WITH THE SAID MATERIALS

BACKGROUND OF THE INVENTION

The present invention relates to the use of the polymeric materials for enlarging a human glans and a method of performing a surgery for enlarging a human glans with any of the said materials.

A sexual intercourse of an animal is a manifestation of the primitive instinct of the animal originating from its instinct of preservation of the species; however humans can have a sexual intercourse quite voluntarily at any time without any estrous cycle, which is a characteristic intrinsic to human alone. It can be hardly denied that the sexual intercourse is a very important part of physical and mental health in their life, not as the instinct of preservation of the species. It is thought that the sexual intercourse is an extremely primitive and fundamental nature of the love for maintaining and advancing the group society of each animal. A certain scholar even said that nothing but the sexual intercourse could make people feel happy both mentally and physically without any adverse effect.

A narcotic for an extremely pleasant sensation is said to give a physical and mental comfort, but it is much deficient in perfectness of satisfaction. Moreover, it goes without saying that its side effects have an enormous evil influence.

According to the old Chinese sexual literatures, a male genital organ can function best only under the following conditions;

first: the genital organ should be stiff;

second: the genital organ should be warm;

third: the glans should be large; and fourth: the penis should be thick and long.

The old Japanese, Indian or Arabian sexual classics attach great importance to the size of the glans, rather than to the lenghth or the thickness of the penis. That is to say, they thought that a big glans, rather than a long or thick penis, was absolutely important in order for a male genital organ to enhance a pleasant sensation of a female mate and further give a satisfaction to her.

Since the sexual intercourse is thought to be so important, various efforts have been exerted to reinforce the male sexual function. However, most of such efforts have been focused on enlargement of the genital organ, while there has been no attempt to enlarge the glans in thickness.

A male glans is covered with a thin mucosa, and it comprises of corpus spongiosum which is full of blood just below the mucosa without any subcutaneous soft tissue layer existing in the general skin. For that reason, it has been thought that it is impossible to modify the glans shape. It has been, therefore, perceived that no method will be available for enlarging the glans, and such perception has led to no attempt to enlarge the glans so far.

SUMMARY OF THE INVENTION

The present inventor has studied the glans for a long period, and observed the glans histologically. As a result, it has been concluded that any polymeric material harmless to the human body and not well absorbed into the somatic tissue can be transplanted into a layer referred to as the lamina propria mucosae. It functions as a dermal layer of the skin, which is at least 2~3 mm thick between the epithelial layer of the mucosa and the corpus spongiosum in the glans. After transplantation, the radius of the glans corona can be enlarged by 0.5~3.0 mm, preferably 1.0~2.0 mm, and such enlargement of the glans will enable men who are possessed by psychological inferiority complex about their small glans to gain confidence in their sexual life, further giving sexual satisfaction to their female mate by nodular stimulating the vaginal wall during the sexual intercourse.

Under this conclusion, the present invention has been made perfectly.

DETAILED DESCRIPTION OF THE INVENTION

The present invention is described in details as follows;

Polymeric materials harmless to the human body and not well absorbed into the somatic tissue is used in the present invention. It includes collagen, artecoll (trade name), dermalive (trade name), zyplast (trade name), perlane (trade name), hyaluronic acid and restylane (trade name). These materials have been used as an insertion into the human body for removing fine wrinkles or correcting recess regions in the skin, but their use for enlarging the glans have never been examined nor attempted so far.

Description of Available Materials

Collagen is a kind of protein and a constituent element of muscle, bone and skin.

Artecoll is a suspension of polymethyl-metacrylate of a micro global form in 3.5% collagen solution at a ratio of 1:3. The surfaces of the micro small globes are very smooth and uniform, and their purity is high. Each micro globe is 30~40 μm in diameter.

Hyaluronic acid is a major element constituting the animal tissue, particularly the cartilage of birds. It is a significant component of the bio-tissue which is found even in the plant species.

Dermalive (trade name) comprises soft and non-absorbable fragments of acrylic hydrogel dispersed in hyaluronic acid gel prepared by crosslinking the non-animal hyaluronic acid.

Restylane (trade name) is a consistent elastomer substance which is sterilized and has no pyrogen.

Perlane (trade name) is a peculiar form of the non-animal stabilized hyaluronic acid (NASHA). Perlane does not contain any animal protein.

Zyplast (trade name) contains collagen prepared by crosslinking the cowhide collagen with glutaraldehyde in 0.3% lidocaine solution at a content of 35 mg/ml.

Collagen or hyaluronic acid is used in the state of 1~10% (weight) gel made by dissolving it in water, and preferably in the state of 3~8% (weight) gel.

All the said polymeric materials available for the present invention shall have neither bacteria nor pyrogen therein. It is desirable to transplant any of the said materials by using an injector. The said materials are already used for removing fine wrinkles between one's eyes, dimple scars, wrinkles in the eye rims, facial scars, etc. The said polymeric materials are commercialized in the form of one dose of injection set.

Restylane delays absorption of hyaluronic acid in vivo by crosslinking hyaluronic acid, while zyplast delays absorption of collagen in vivo by crosslinking collagen with glutaraldehyde.

Histological Region for Injection

Any of collagen, restylane, zyplast and hyaluronic acid is usually transplanted by injecting it into the dermis layer.

It is already in public domain that artecoll or dermalive shall be injected into the subdermal region which is a boundary layer between the derma and the subcutaneous fat.

It is also in public domain that if the said transplantation is conducted, with collagen or hyaluronic acid, or crosslinked derivatives of collagen and hyaluronic acid are slowly absorbed in vivo. However, in case of artecoll or dermalive, it may cause the cicatricial tissue, which can keep any filled volume by generating the fibrous tissue from 2~3 months after such transplantation. Consequently, This can cause side effects such as swelling or hardening in the periphery of the transplanted region, and such deformity shall be removed by a proper surgery.

Accordingly, in case artecoll or dermalive is transplanted into the derma layer, polymethyl-metacrylate or acrylic hydrogel thereof may show through derma layer. Also, if the cicatricial tissue resulting from such transplantation is formed excessively, it may get nodular irregularity. Therefore, artecoll or dermalive shall not be transplanted into the derma layer, but into the subdermal region which is a boundary layer between the derma and the subcutaneous fat. If artecoll or dermalive is transplanted, the fibrous connective tissue is generated around polymethyl-metacrylate or acrylic hydrogel thereof, and then, fibrin is formed to generate the cicatricial tissue and consequently, the transplanted region may get to be nodulated.

However, this side effect is rather a merit in the plastic operation for enlarging the glans, because it can enhance a sexual satisfaction.

If any of the said materials for enlarging the glans is transplanted into the lamina propria mucosae just below the mucosa surrounding the glans, the circumference of the glans is increased by the thickness of the transplanted material, and consequently, enlarging the glans.

For example, if it is transplanted into the lamina propria mucosae just below the mucosa surrounding the glans whose radius is 15 mm (diameter:30 mm) so that the transplanted material may be 2 mm thick, the circumference of the glans corona gets is increased by 12.56 mm according to the formula for obtaining a circumference(2 mm×2×3.14). Consequently, the glans becomes considerably larger.

If the circumference of the glans corona gets is equaled to its radius×2 π and the radius of the enlarged glans is 15 mm+2 mm;

Then, the circumference of the glans corona is;

(15 mm+2 mm)×2π=15 mm×3.14+2×2×3.14=47.10 mm+12.56 mm=59.66 mm and section area is increased by about 28%.

If any of the said materials is transplanted into the lamina propria mucosae just below the mucosa surrounding the glans(30 mm), So the transplanted material may be 1.5 mm thick, the circumference of the glans corona is increased by 9.42 mm (1.5 mm×2π=1.5 mm×2×3.14=9.42mm), and the sectional area is also increased by about 21%.

Any of the said materials can be transplanted into a partial or a whole lamina propria mucosae of the glans, but it is preferably transplanted into the lamina propria mucosae of the glans corona.

FIG. 1 is a sectional view of the glans, comprising the glans mucosa (1), the lamina propria mucosae (2), the corpus spongiosum of the glans, the urethra (4) and the corpus spongiosum of the urethra (5). The material as used in this invention is transplanted into the lamina propria mucosae (2).

The present invention is described in more details by the following examples;

EXPERIMENTAL EXAMPLE 1

A total of 28 adult male rabbits having passed puberty were divided into 14 groups, each of which consisted of 2 rabbits. In 7 groups, collagen, hyaluronic acid, artecoll, dermalive, zyplast (trade name), restylane and perlane were respectively injected into the lamina propria mucosae just below the glans mucosa, with each one material injected to each one group. In the other 7 groups, collagen, hyaluronic acid, artecoll, dermalive, zyplast, restylane and perlane were respectively injected into the corpus spongiosum of the glans, with each one material injected to each one group. Then, a pathological biopsy was conducted on the glans, the penis, etc. of each group at the 2nd and 4th week after the said injection, in order to observe for any side-effects or complications such as development of embolus in the draining vein of the corpus spongiosum in the penis and the glans, variation in the tissue, inflammation of the lymph node, movement of the transplanted material, foreign body reaction, etc.

As a result of the said experiment, complications such as development of embolus in the draining vein of the corpus spongiosum in the penis and the glans, variation in the tissue, inflammation of the lymph node, or foreign body reaction, etc. was not observed.

EXPERIMENTAL EXAMPLE 2

Then, in order to verify the sexual function of the said adult male rabbit, whose glans was enlarged in Example 1, it was mated with an adult female rabbit. As a result, the female rabbit was found to be pregnant. Consequently, it was verified that there was no trouble in the sexual function of the said adult male rabbit.

EXPERIMENTAL EXAMPLE 3

A total of 14 adult male volunteers were divided into 7 groups, each of which consisted of 2 volunteers. Collagen, hyaluronic acid, artecoll, dermalive, zyplast, restylane and perlane were respectively injected into the lamina propria mucosae of the glans corona so that each injected material may be 1.5 mm thick exactly, with each one material injected to each one group. Then, the male subjects reserved sexual intercourse with their respective adult female mates from 7 days after such injection. As a result, no trouble was found out in the erectile function of the male subjects, and further it was reported that both the male subjects and their female mates had a considerably greater sexual satisfaction.

According to their female mates, 1. they felt that the male genital organ was nodular stimulating the vagina wall;
2. they could surely feel that the glans of the male genital organ was enlarged; and
3. they felt that a small bead seemed to be rolling in the vagina.

It was reported that they could, therefore, have a great sexual satisfaction.

As a result of the said experiments, it was identified that collagen, hyaluronic acid, artecoll, dermalive, zyplast, restylane and perlane could be used as a transplantable material in the surgery of enlarging the glans of the male genital organ. Also, both the male subjects and their female mates had a great sexual satisfaction after the surgery of enlarging the glans. Particularly, it was noted that their female mates felt much more satisfied sexually.

What is claimed is:

1. A method of enlarging the glans of the male genital organ by injecting an implantable polymeric material into the lamina propria mucosae of the glans in order to enlarge the glans of the male genital organ, wherein said polymeric material is selected from the group consisting of collagen, hyaluronic acid, dermalive, zyplast, restylane and perlane.

2. The method of claim 1, wherein the implantable polymeric material implanted into the lamina propria mucosae of the male genital is 0.5 mm –3.0 mm thick.

3. The method of claim 1 or 2, wherein the implantable polymeric material is injected into the lamina propria mucosae of the glans corona of the male genital organ.

* * * * *